(12) United States Patent
Park et al.

(10) Patent No.: US 7,606,625 B2
(45) Date of Patent: Oct. 20, 2009

(54) METHOD AND DEVICE FOR ALIGNING A STENT WITH A STENT SUPPORT

(75) Inventors: Sang joon Park, Waterloo (CA); Shaulaine Choo, Cambridge (CA); Anthony S. Andreacchi, San Jose, CA (US); Yung-Ming Chen, Cupertino, CA (US); Arnoldo M. Currlin, San Diego, CA (US); Antonio Garcia, San Jose, CA (US); Jason Van Sciver, Los Gatos, CA (US); Thomas David Esbeck, Murrieta, CA (US); Bryan D. Glenn, Murrieta, CA (US)

(73) Assignees: Abbott Cardiovascular Systems Inc., Santa Clara, CA (US); ATS Automation Tooling Systems Inc., Ontario (CA)

( * ) Notice: Subject to any disclaimer, the term of this patent is extended or adjusted under 35 U.S.C. 154(b) by 209 days.

(21) Appl. No.: 11/764,015

(22) Filed: Jun. 15, 2007

(65) Prior Publication Data

US 2008/0312728 A1 Dec. 18, 2008

(51) Int. Cl.
*G05B 13/02* (2006.01)
*A61F 2/06* (2006.01)
*G06F 19/00* (2006.01)
*A61F 5/04* (2006.01)

(52) U.S. Cl. .............. 700/57; 700/56; 700/60; 700/186; 700/192; 600/374; 600/381; 623/1.11; 623/1.17

(58) Field of Classification Search .......... 623/1.11, 623/1.15, 1.16, 1.17; 600/374, 381, 407; 700/56–60, 117, 159–160, 186, 192, 195
See application file for complete search history.

(56) References Cited

U.S. PATENT DOCUMENTS 5,630,830 A * 5/1997 Verbeek ............... 606/198

(Continued)

FOREIGN PATENT DOCUMENTS

DE 100 32 398 2/2001

(Continued)

OTHER PUBLICATIONS

U.S. Appl. No. 10/255,913, filed Sep. 26, 2002, Tang et al.

(Continued)

*Primary Examiner*—Ramesh B Patel
(74) *Attorney, Agent, or Firm*—Squire, Sanders & Dempsey, L.L.P.

(57) ABSTRACT

A method for aligning a stent with a stent support includes the steps of (1) placing a stent support and a stent mounted on the stent support in a vertically position with the stent support's first support element at a lower position and the stent support's second support element at an upper position; (2) obtaining a digital image of the stent support and stent; (3) analyzing the digital image of the stent support and stent to compute the vertical position of the stent's upper end; (4) computing a desired position of the second support element based on the position of the stent's upper end; and (5) using a positioning device to move the second support element to the desired position. The movement of the second support element causes the conical sections of the first and second support elements to engage the respective ends of the stent to center the stent around a core element of the stent support and to secure the stent in a longitudinal direction of the stent support.

30 Claims, 16 Drawing Sheets

U.S. PATENT DOCUMENTS

| | | | |
|---|---|---|---|
| 5,897,911 A | 4/1999 | Loeffler | |
| 6,161,029 A * | 12/2000 | Spreigl et al. | 600/381 |
| 6,527,863 B1 | 3/2003 | Pacetti et al. | |
| 6,575,994 B1 * | 6/2003 | Marin et al. | 606/198 |
| 7,390,524 B1 * | 6/2008 | Chen | 427/2.24 |
| 7,402,329 B2 | 7/2008 | Pacetti et al. | |
| 7,404,979 B1 | 7/2008 | Pacetti | |
| 2006/0035012 A1 | 2/2006 | Pacetti et al. | |
| 2007/0003688 A1 | 1/2007 | Chen et al. | |
| 2007/0073134 A1 * | 3/2007 | Teichman et al. | 600/407 |
| 2008/0087474 A1 | 4/2008 | Nufer et al. | |
| 2008/0280025 A1 * | 11/2008 | Scheer | 427/2.24 |
| 2008/0307668 A1 | 12/2008 | Watterodt et al. | |
| 2008/0311280 A1 | 12/2008 | Rego et al. | |
| 2008/0311281 A1 | 12/2008 | Andreacchi et al. | |
| 2008/0312747 A1 | 12/2008 | Cameron et al. | |
| 2008/0312869 A1 * | 12/2008 | Hemphill et al. | 702/173 |

FOREIGN PATENT DOCUMENTS

| | | |
|---|---|---|
| EP | 1 195 584 | 4/2002 |
| WO | WO 2007/130257 | 11/2007 |

OTHER PUBLICATIONS

U.S. Appl. No. 10/750,312, filed Dec. 30, 2003, Desnoyer et al.

U.S. Appl. No. 10/805,047, filed Mar. 18, 2004, Yip et al.

U.S. Appl. No. 11/193,849, filed Jul. 28, 2005, Harold et al.

International Search Report and the Written Opinion, for PCT/US2008/061806, mailed Dec. 5, 2008, 19 pgs.

Invitation to pay additional fees, including communication relating to the results of the partial international search, for PCT/US2008/061806, mailed Aug. 27, 2008, 9 pgs.

* cited by examiner

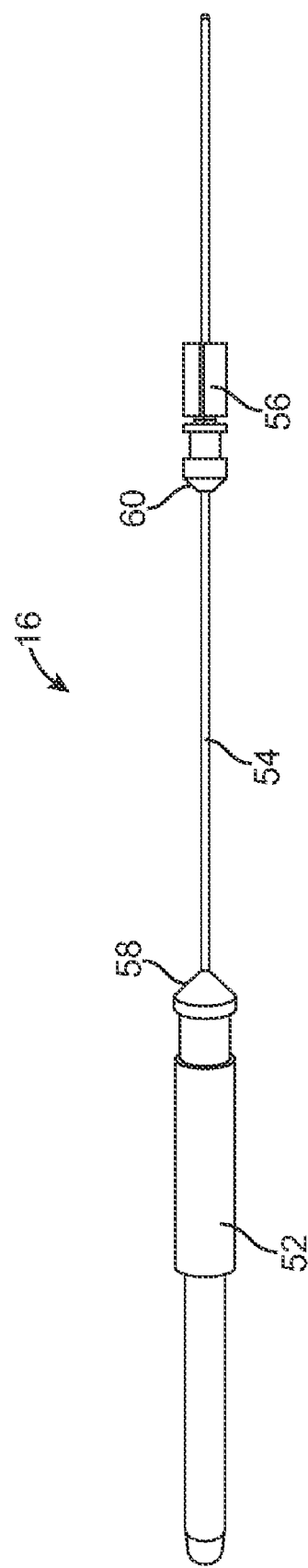

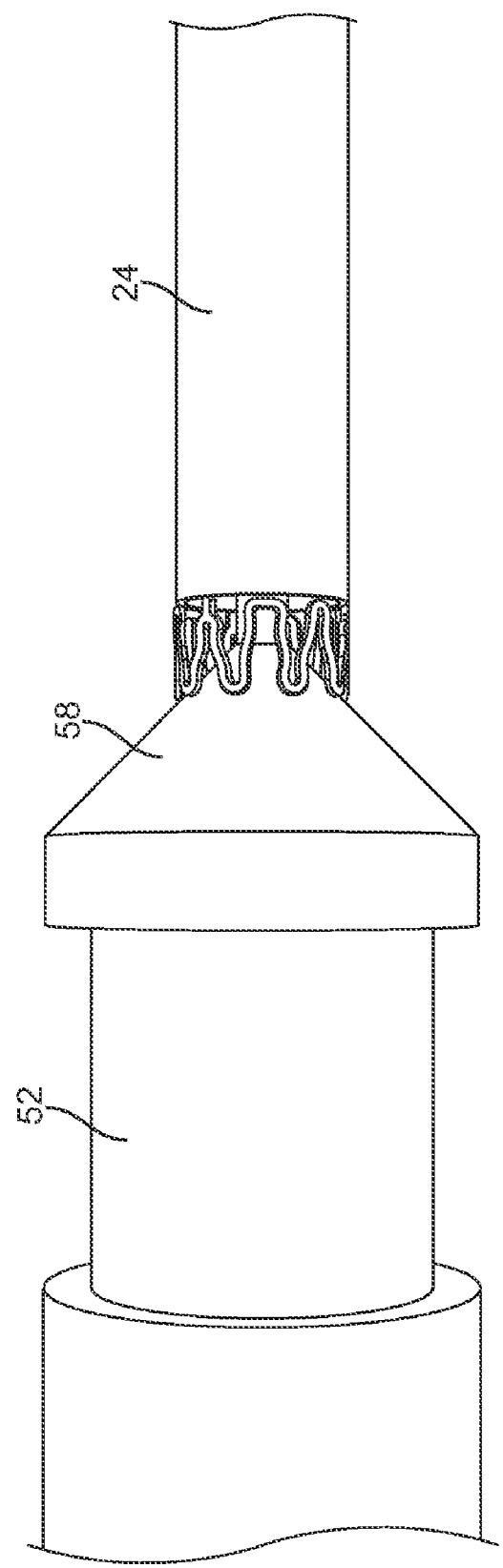

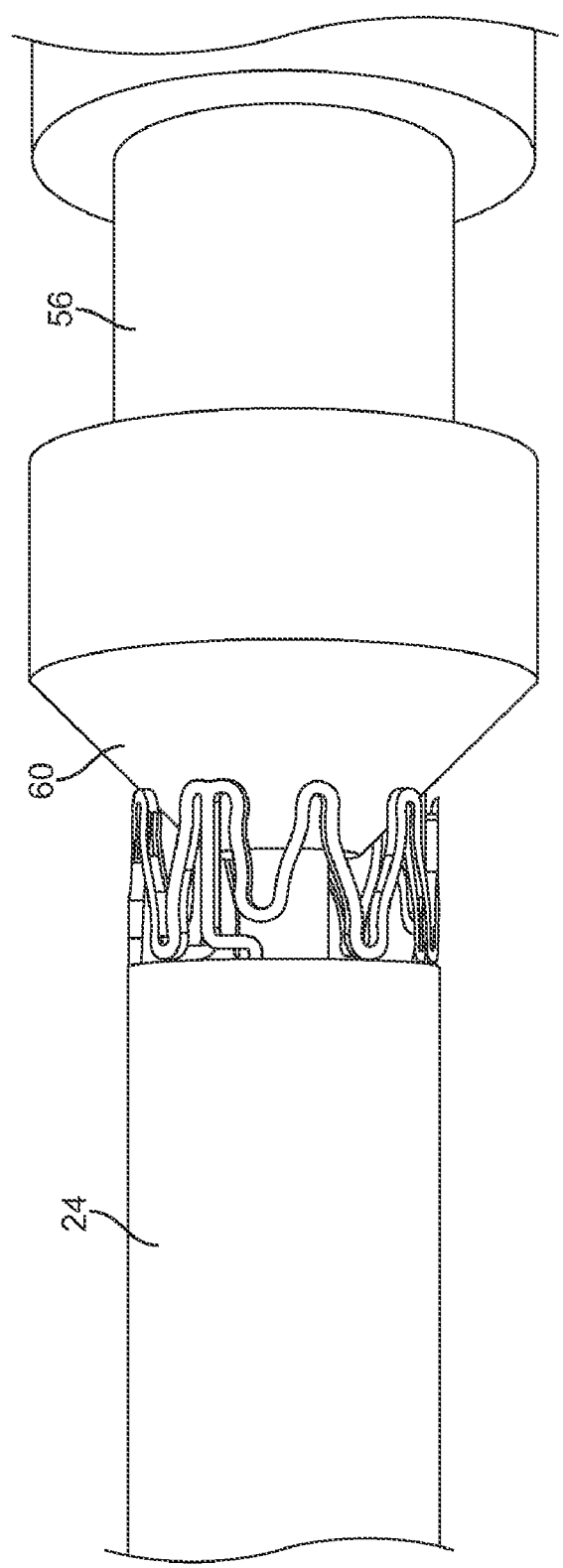

METHOD AND DEVICE FOR ALIGNING A STENT WITH A STENT SUPPORT

FIELD OF THE INVENTION

This invention relates to a method and device for aligning a stent with a stent support.

BACKGROUND

In the last several years, minimally invasive surgical procedures, such as percutaneous transluminal coronary angioplasty (PTCA), have become increasingly common. A PTCA procedure involves the insertion of a catheter into a coronary artery to position an angioplasty balloon at the site of a stenotic lesion that is at least partially blocking the coronary artery. The balloon is then inflated to compress the stenosis and to widen the lumen in order to allow an efficient flow of blood through the coronary artery.

Following PTCA and other stenotic treatment procedures, a significant number of patients experience restenosis or other vascular blockage problems. These problems are prone to arise at the site of the former stenosis.

In order to help avoid restenosis and other similar problems, a stent may be implanted into the vessel at the site of the former stenosis with a stent delivery catheter. A stent is a tubular structure which is delivered to the site of the former stenosis or lesion and compressed against vessel walls thereat, again with a balloon. The structure of the stent promotes maintenance of an open vessel lumen. The stent can be implanted in conjunction with the angioplasty.

Stents can also be used to provide for local delivery of agents. For example, radiotherapy and drug delivery treatments applied to the site of the former stenosis following angioplasty have been found to aid in the healing process and to reduce significantly the risk of restenosis and other similar problems. Local delivery of agents is often preferred over systemic delivery of agents, particularly where high systemic doses are necessary to achieve an effect at a particular site. High systemic doses of agents can often create adverse effects. One proposed method of local delivery is to coat the surface of a stent with an agent.

A stent is typically coated with a primer layer and an agent layer. The primer layer is applied between the stent and the agent layer to improve adhesion of the agent layer to the stent. In some cases, the agent layer may be applied directly to the stent.

Spray coating is commonly used to apply a layer of coating to a stent. A spray coating apparatus typically includes a spray nozzle and a pump that supplies a coating substance from a reservoir to the spray nozzle. The coating substance is ejected through the nozzle to create a plume of coating substance.

During coating operation the stent is supported by a stent support, and the stent support and stent rotate about the axis of the stent support. The stent support is also configured to axially or linearly translate the stent through the plume of coating substance. The nozzle may be translated along the axis of the stent as an alternative to or in addition to axially translating the stent. The coating substance is deposited on the stent as the stent is translated through the plume of the spray nozzle from one end of the stent to the other end. After a selected number of passes through the plume, the deposited coating substance is allowed to dry or subjected to a drying process prior to further spraying of coating substance. The spraying and drying steps are repeated until a desired amount of coating substance is deposited on the stent.

The coating substance ejected by the nozzle is not uniformly distributed in the plume of the spray nozzle. The concentration of coating substance is highest in the areas along or near the longitudinal axis of the nozzle. As the distance from the axis of the nozzle increases, the concentration of coating substance decreases.

To increase the efficiency of coating operation, it is desirable to place the stent in an area of the plume that has a high concentration of coating substance, i.e., an area along or near the axis of the nozzle. To ensure that the stent remains in the desired area of the plume, it is important for the axis of the stent to be aligned with the axis of the stent support. If the stent support and stent are not coaxial, the stent will oscillate about the axis of the stent support during rotation, causing the stent to move in and out of the area of the plume with a high coating substance concentration. This will not only decrease the efficiency of coating operation but also produce an uneven coating pattern on the stent surface.

Additionally, misalignment between the stent axis and the stent support axis may cause inconsistent application of coating substance to the stents, with stents placed near the axis of the nozzle receiving more coating substance than stents placed relatively far from the axis of the nozzle. This variation in the amount of stent coating may increase the number of stents having coating weights outside of the acceptable range, thereby increasing the stent defective rate. These variations are difficult to compensate by adjusting the rate or duration of spray, because the misalignment is unpredictable.

Currently there are no efficient and reliable methods to ensure a proper alignment of a stent with a stent support.

SUMMARY

The method and device of the present invention can reliably, efficiently and precisely mount a stent on a stent support with a proper alignment of the axes of the stent and stent support.

According to one aspect of the invention, a method for aligning a stent with a stent support includes the steps of (1) placing a stent support and a stent mounted thereon in a vertical position with the stent support's first support element at a lower position and the stent support's second support element at an upper position, (2) obtaining a digital image of the stent support and stent, (3) analyzing the digital image of the stent support and stent to compute the vertical position of the stent's upper end, (4) computing a desired position of the second support element based on the position of the stent's upper end, and (5) using a positioning device to move the second support element to the desired position. The movement of the second support element causes the conical sections of the first and second support elements to engage the respective ends of the stent to center the stent around a core element of the stent support and to secure the stent in a longitudinal direction of the stent support.

Before the image of the stent support and stent is taken, it is preferable to re-seat the stent on the conical portion of the first support element to ensure that the stent is seated properly. There are many different ways to re-seat a stent. For example, if the stent is not seated properly, a light strike to the first support element may cause the stent to seat properly. Alternatively, the first support element can be vibrated to re-seat the stent. Re-seating may also be accomplished by lifting the stent off the first support element and releasing the stent to allow the stent to reengage with the conical portion of the first support element under the weight of the stent. Additionally, the stent can be manipulated, such as tapped, to re-seat the stent.

After the step of moving the second support element of the stent support to the desired position, the stent runout may be determined to ensure that it is less than an acceptable limit. The term "runout" is defined as the degree to which the axis of the stent deviates from the axis of the first support element of the stent support. The stent runout can be computed from one or more digital images of the stent support and stent. If the computed stent runout is greater than the acceptable limit, the second support element may be lifted to disengage the second support element with the upper end of the stent, and the process may be repeated to position the second support element at the desired position. Alternatively, the stent may be considered defective and discarded.

Additionally or alternatively, a digital image of the stent support and stent may be taken to compute the actual position of the second support element. The actual and desired positions of the second support element may be compared. If the difference between the actual and desired positions of the second support element exceeds an acceptable limit, the positioning device will again attempt to move the second support element to the desired position. This process can be repeated until the difference between the actual and desired positions of the second support element no longer exceeds the acceptable limit.

In some cases, it may be desirable to ensure that the stent is properly oriented on the stent support. This means that one end of the stent points in the direction of the first support element and the other end points in the direction of the second support element. The orientation of the stent can be determined from the types of end crowns at one or both ends of the stent.

A stent manufacturer often makes more than one type of stents. It may be desirable in some cases to verify that the proper type of stent is mounted on the stent support. The stent type may be determined in various manners. For example, the length of the stent can be computed from the digital image and can be used to determine the type of the stent mounted on the stent support. Or the number of crowns at a stent end may be computed from the digital image and can be used to determine the type of the stent. Alternatively, the types of crowns at a stent end may be used to determine stent type. In some cases, one or more of these stent features may be used together to determine stent type.

To facilitate the determination of the number of crowns and the types of crowns at a stent end, the digital image preferably includes a 360° view of the outer surface of the stent or stent end.

Preferably, the free end of the stent support's core element, i.e., the end of the core element not connected to the first support element, is affixed so that the core element and the first support element are substantially coaxial. This way, the position of the core element in the digital image is always known, and it is easier to determine the position of the stent from the digital image.

According to another aspect of the invention, a device for aligning a stent with a stent support includes a stent support receptacle for receiving a first support element of a stent support to position the stent support in a vertical position, a digital imaging device for imaging a stent mounted on the stent support, a computer, and a positioning device for moving a second support element of the stent support to the desired position. The computer can be used to compute the position of an upper end of the stent from a digital image of the stent support and stent and to compute a desired position of the second support element of the stent support based on the position of the stent's upper end. The computer can also be used to compute stent runout, stent type and stent orientation.

In a preferred embodiment, the device for aligning a stent with a stent support further includes a core element support for supporting a free end of a core element of the stent support so that the core element and the first support element are substantially coaxial.

BRIEF DESCRIPTION OF THE DRAWINGS

FIG. 4 is a perspective view of a stent support.

FIGS. 5A and 5B are perspective views showing the conical portions of the first and second support elements of a stent support supporting the ends of a stent.

DETAILED DESCRIPTION OF PREFERRED EMBODIMENTS

Figure 1:
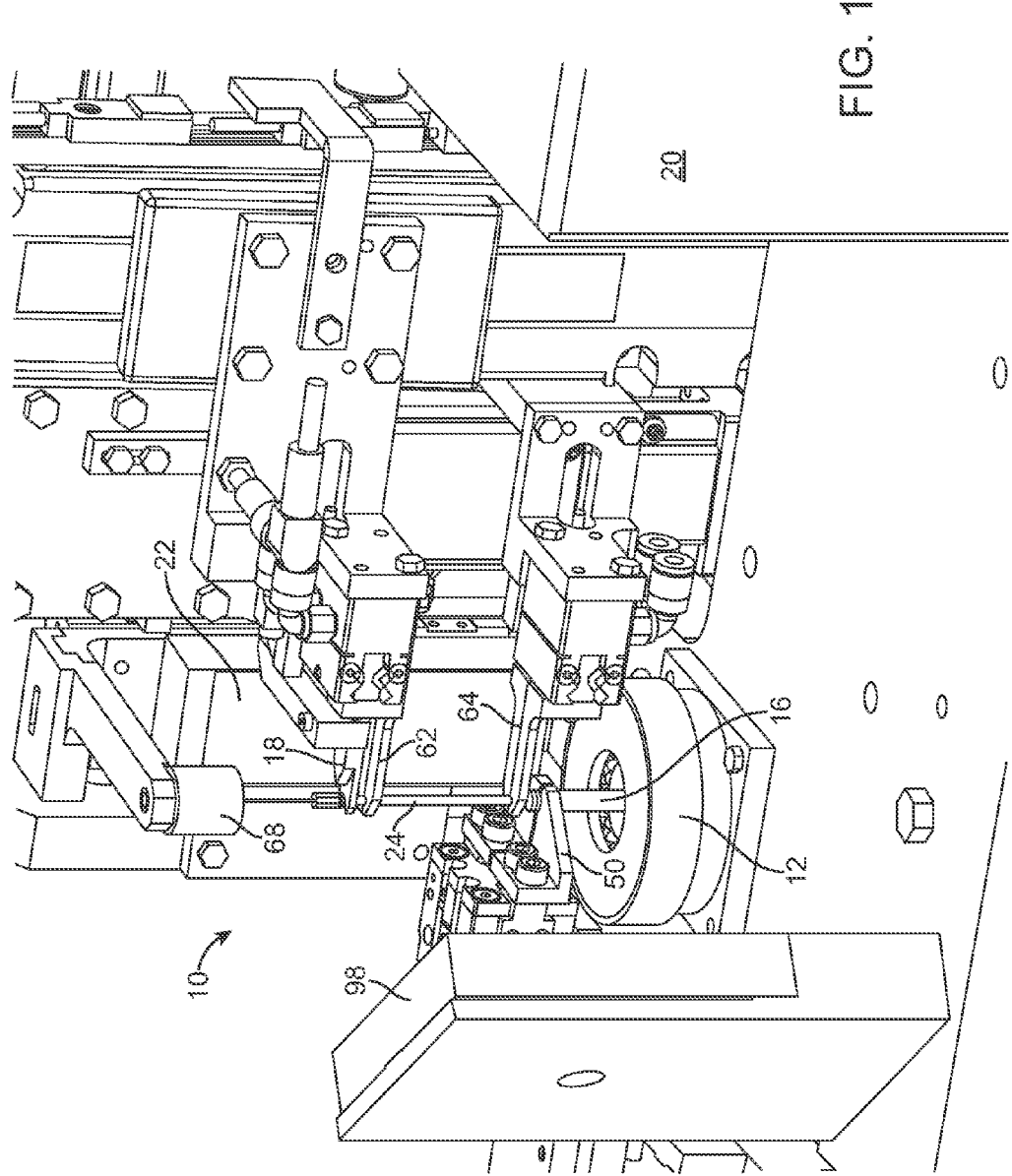
FIG. 1 is a perspective view of an exemplary device of the present invention for mounting a stent on a stent support in a way that reduces stent runout.

One aspect of the present invention relates to a device for precisely and efficiently mounting a stent on a stent support in a way that reliably reduces stent runout. FIG. 1 illustrates an exemplary device 10 of the present invention. The device 10 includes a stent support receptacle 12 for receiving a stent support 16 to position the stent support 16 in a vertical position; a digital imaging device 20, such as a digital camera; a computer 14 (FIG. 13); and a positioning device 18. The device 10 may include additional components, as shown in FIG. 1, which will be described hereinafter.

A stent used with the present invention may have any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. Embodiments of the present invention are applicable to virtually any stent design and are, therefore, not limited to any particular stent design or pattern. One embodiment of a stent pattern may include cylindrical rings composed of struts. The cylindrical rings may be connected by connecting struts.

In some embodiments, a stent may be formed from a tube by laser cutting the pattern of struts in the tube. The stent may also be formed by laser cutting a metallic or polymeric sheet, rolling the pattern into the shape of the cylindrical stent, and providing a longitudinal weld to form the stent. Other methods of forming stents are well known and include chemically etching a metallic or polymeric sheet and rolling and then welding it to form the stent.

Figure 2:
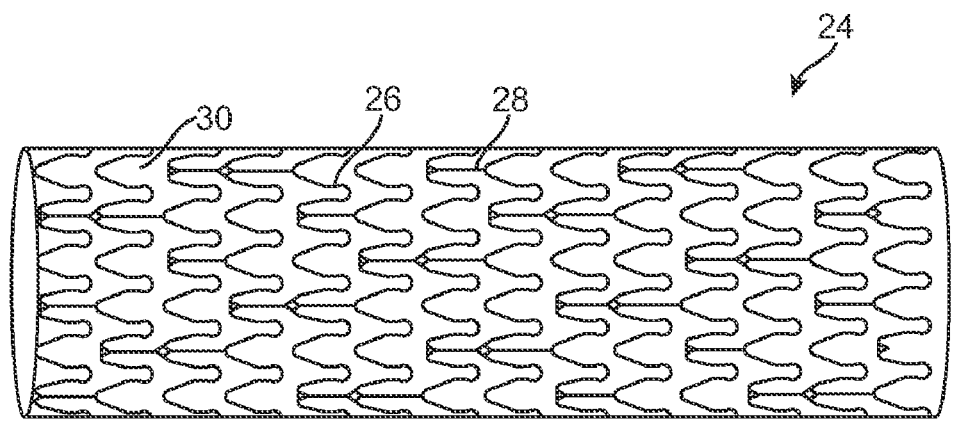
FIG. 2 is a perspective view of a cylindrically-shaped stent.

FIG. 2 illustrates a stent 24 formed from a plurality of struts 26. The plurality of struts 26 are radially expandable and interconnected by connecting elements 28 that are disposed between adjacent struts 26, leaving lateral openings or gaps 30 between adjacent struts 26. The struts 26 and connecting elements 28 define a tubular stent body having an outer, tissue-contacting surface and an inner surface.

The cross-section of the struts 26 in the stent 24 may be rectangular- or circular-shaped. The cross-section of struts is not limited to these, and therefore, other cross-sectional shapes are applicable with embodiments of the present invention. Furthermore, the pattern should not be limited to what has been illustrated as other stent patterns are easily applicable with embodiments of the present invention.

A stent may be coated with any number of layers. For example, the coating of a stent may comprise one or more of the following four types of layers:

(a) an agent layer, which may comprise a polymer and an agent or, alternatively, a polymer free agent;

(b) an optional primer layer including one or more polymers, which layer may improve adhesion of subsequent layers on the implantable substrate or on a previously formed layer;

(c) an optional topcoat layer, which may serve as a way of controlling the rate of release of an agent; and (d) an optional biocompatible finishing layer, which may improve the biocompatibility of the coating.

The agent layer may be applied directly to a stent as a pure agent. Alternatively, the agent can be combined with a biodegradable polymer as a matrix, wherein agent may or may not be bonded to the polymer. The optional primer layer may be applied between the implantable substrate and the agent layer to improve adhesion of the agent layer to the implantable substrate and can optionally comprise an agent. A pure agent layer can be sandwiched between layers comprising biodegradable polymer. The optional topcoat layer may serve as a membrane to control the rate of release of the bioactive agent and can optionally comprise agent. The biocompatible finishing layer may also be applied to increase the biocompatibility of the coating by, for example, increasing acute hemocompatibility and can also comprise an agent.

The polymers in the agent layer and optional primer layer can be biostable, bioabsorbable, biodegradable, or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

The therapeutic agent can include any substance capable of exerting a therapeutic or prophylactic effect. Examples of therapeutic agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S.A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin.

Figure 3:
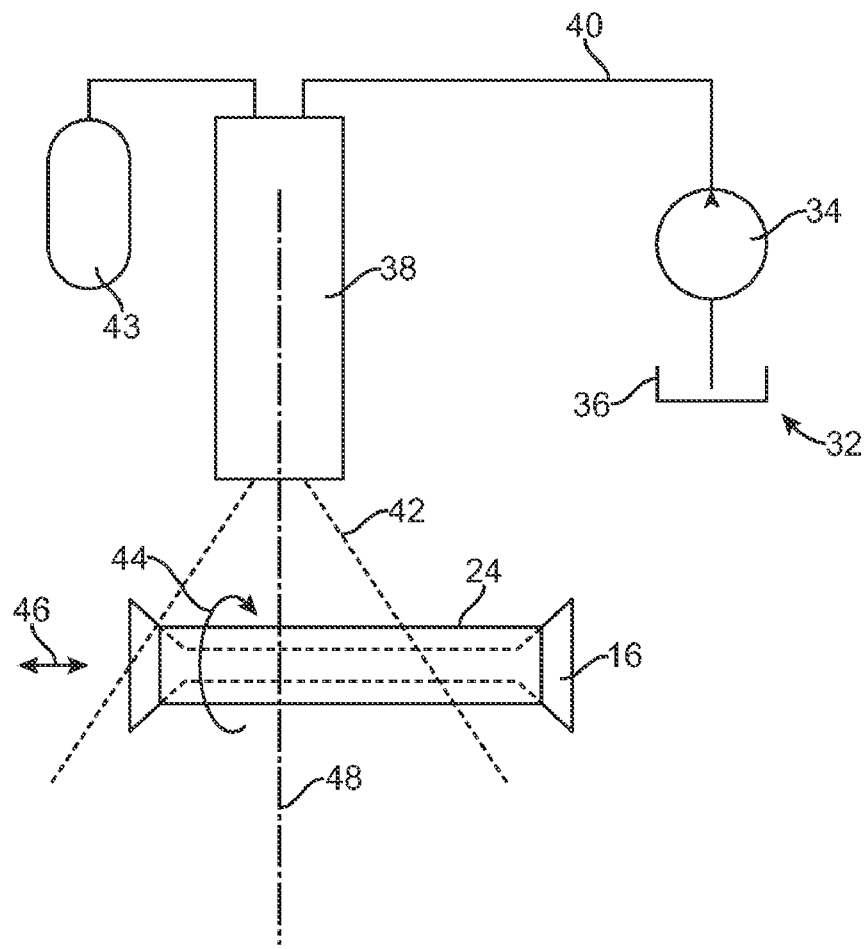
FIG. 3 is a schematic diagram for a spray coating apparatus.

Spray coating is commonly used to apply a coating layer to a stent. Spray coating a stent typically involves mounting a stent on a stent support, followed by spraying a coating substance from a nozzle onto the mounted stent. FIG. 3 depicts a spray coating apparatus 32 for coating a stent 24. In this apparatus, a pump 34 supplies a coating substance from a reservoir 36 to a spray nozzle 38 through a hose 40. The coating substance is ejected through the nozzle 38 to create a plume 42 of coating substance. The nozzle 38 preferably is a gas-assisted external mixing atomizer, which atomizes the coating substance with gas supplied by a gas supply 43.

The coating substance is not uniformly distributed in the plume 42 of the spray nozzle 38. The concentration of coating substance is highest in the areas along or near the axis 48 of the nozzle 38. As the distance from the axis 48 of the nozzle 38 increases, the concentration of coating substance decreases. In other words, there are more coating substance droplets per unit of volume in the areas along or near the axis 48 of the nozzle 38 than in the areas near the periphery of the plume 42.

During coating operation the stent 24 is supported on a stent support 16, and the stent support 16 and stent 24 rotate about the axis of the first support element 52 (FIG. 3), as shown by an arrow 44. The speed of rotation can be from about 0.1 rpm to about 300 rpm, more narrowly from about 30 rpm to about 200 rpm. By way of example, the speed of rotation can be about 150 rpm.

Preferably, the stent support 16 and stent 24 are axially or linearly translated through the plume 42, as shown by an arrow 46. Alternatively or additionally, the nozzle 38 can be translated along the axis of the stent 24. The coating substance is deposited on the stent 24 as the stent 24 is translated through the plume 42 of the spray nozzle 38 from one end to the other end of the stent 24. After a selected number of passes through the plume 42, the deposited coating substance is allowed to dry or subjected to a drying process prior to further spraying of coating substance. The spraying and drying steps can be repeated until a desired amount of coating substance is deposited on the stent 24. The nozzle or the stent can be moved at about 1 mm/second to about 12 mm/second, for example about 6 mm/second.

Referring to FIG. 4, a stent support 16 may include a first support element 52, a core element 54, and a second support element 56. The stent support may be, for example, a stent mandrel or stent fixture. The first support element of the stent support may be, for example, a shank. The second support element of the stent support may be, for example, a collet. The first support element 52 may be connected to a motor (not shown) to provide rotational motion about the longitudinal axis of the first support element 52 during coating.

The first support element 52 preferably includes a conical portion 58, tapering inwardly at an angle of, for example, about 15° to about 75°, more narrowly from about 30° to about 60°. In some cases, the angle can be about 45°. In the illustrated embodiment, a first end of the core element 54 is permanently affixed to the conical portion 58 of the first support element 52. Alternatively, the first support element may include a bore for receiving an end of the core element, and the end of the core element may be threaded to screw into the bore.

The second support element 56 also includes a conical portion 60 having an inwardly tapered angle which can be the same as or different from the tapered angle of the first support element's conical portion 58. The second support element 56 has a through bore. A second end (free end) of the core element 54 can extends into the through bore of the second support element 56 and can be press-fitted or friction-fitted within the bore to prevent the second support element 56 from freely moving on the core element 54.

The stent support 16 supports the stent 24 via the conical portions 58, 60 of the first and second support elements 52, 56. FIG. 5A shows that the conical portion 58 of the first support element 52 supports one end of the stent 24, and FIG. 5B shows that the conical portion 60 of the second support element 56 supports the other end of the stent 24. In FIGS. 5A and 5B and in subsequent Figures, only the struts in the end rings of the stent are shown, and the struts in the rest of the stent are not shown. As the conical portions 58, 60 of the first and second support elements 52, 56 are advanced towards each other, they automatically cause the stent 24 to become centered about the core element 54, and they also secure the stent 24 in the longitudinal direction of the stent support 16. The only contact between the stent 24 and the stent support 16 is at the interface between the conical portions 58, 60 and the inner rims at the ends of the stent 24. At least one of the conical portions 58, 60 may have a roughened surface to absorb excess coating substance.

To reduce stent runout, the opposing forces exerted by the first and second support elements 52, 56 to secure the stent 24 preferably are sufficient but not excessive. First, the opposing forces preferably are sufficient to prevent any significant movement of the stent 24 on the stent support 16. If the stent 24 moves relative to the stent support 16 during coating operation, the stent 24 will not remain in a desired area of the plume with a high coating substance concentration. Instead the stent 24 will oscillate about the axis of rotation (i.e., the axis of the first support element 52), causing the stent 24 to move in and out of the area of the plume with a high coating substance concentration.

Additionally, to ensure that the coating is evenly applied to the stent surface, it is preferable that the stent 24 is rotationally secured to, and rotates together with, the stent support 16 during coating operation. If the stent 24 slips rotationally relative to the stent support 16, the stent 24 will not be rotating at a constant speed. As a result, some areas of the stent surface may be exposed to the coating spray for a longer period of time than other areas, resulting in an even coating on the stent surface. The stent 24 is rotationally secured to the stent support 16 by the frictional forces between the stent ends and the support elements 52, 56 of the stent support 16, and the frictional forces are a function of the opposing forces. Thus, the opposing forces preferably are sufficient to ensure that the stent 24 is rotationally secured to the stent support 16 during coating operation.

Second, the opposing forces preferably are not excessive. Excessive forces applied to the ends of the stent 24 may cause the stent 24 to bend and the middle section of the stent 24 to bow out. When the stent support 16 is rotated, the bowed out middle section of the stent 24 may move in and out of the area of the plume with a high coating substance concentration. Since the opposing forces are largely a function of the position of the second support element 56, the desired stent support forces can be achieved by adjusting the position of the second support element 56.

Additionally, insufficient or excessive opposing forces may increase the number or severity of coating defects on the stent's end crowns 106 (FIGS. 15 and 16). If the opposing forces are insufficient, there may be a gap between an end crown 106 of the stent 24 and the conical portion 58, 60 of a support element 52, 56, and coating material may accumulate in the gap. When the stent 24 is moved relative to the conical portion 58, 60, the dry coating material in the gap may stick to the end crown 106, causing excessive coating material on the crown 106. Alternatively, the dry coating material in the gap may stick to the conical surface 58, 60, causing insufficient coating material on the crown 106. Excessive opposing forces may also lead to excessive coating material between an end crown 106 and the conical portion 58, 60, because they may increase the contact area between the end crown 106 and the conical portion 58, 60. An increased contact area may increase the coating material accumulated between the end crown 106 and the conical portion 58, 60. The increased accumulation of coating material, as described above, are more likely to cause stent coating defects.

It should be noted that, in some embodiments of the present invention, the conical portion 58, 60 of each support element 52, 56 may include one or more features that reduce the contact between the conical portion 58, 60 and the end crowns 106 of the stent 24. For example, each conical portion 58, 60 may include ridges that extend from the base of the conical portion 58, 60 to its apex. Preferably, the ridges are dimensioned and spaced so that when a stent end engages the conical portion 58, 60, the crest of each crown 106 engages the crest of a ridge. This further reduces the contact between the conical portion 58, 60 and the end crowns 106 of the stent 24.

Figure 6:
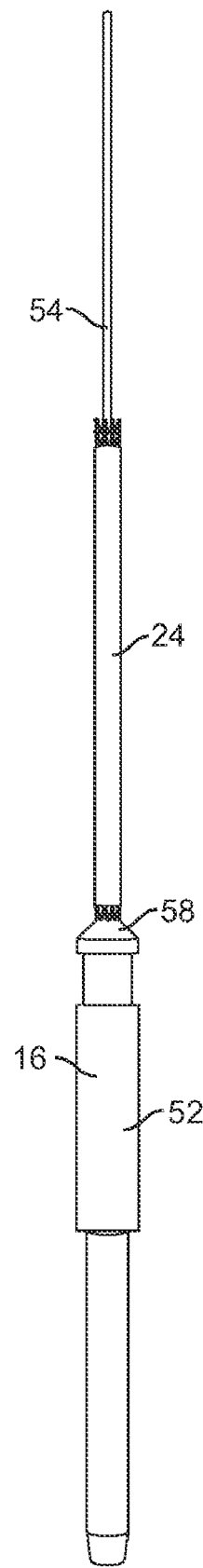
FIG. 6 is a perspective view of a stent mounted on the core element of a stent support without the second support element of the stent support.
Figure 7:
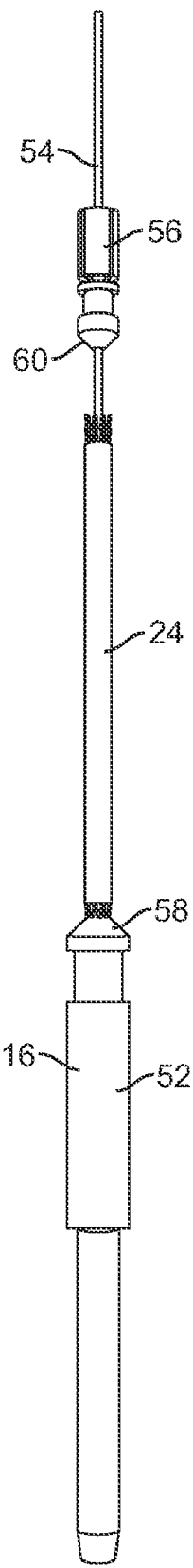
FIG. 7 is a perspective view of a stent mounted on the core element of a stent support with the second support element of the stent support.

Another aspect of the present invention relates to a method for mounting a stent on a stent support to achieve optimum opposing forces and to reliably and efficiently reduce stent runout. In a preferred embodiment of this method, as shown in FIG. 6, the stent 24 is first mounted on the core element 54 of the stent support 16 by extending the core element 54 through the hollow center of the stent 24. Then the second support element 56 is also mounted on the core element 54, as shown in FIG. 7. At this point, the stent 24 is placed between the first and second support elements 52, 56, but the second support element 56 is not advanced far enough to pinch the stent 24 between the first and second support elements 52, 56. The distance between the first and second support elements 52, 56 is greater than the length of the stent 24, and the stent 24 is free to move along the core element 54 between the first and second support elements 52, 56.

Figure 8:
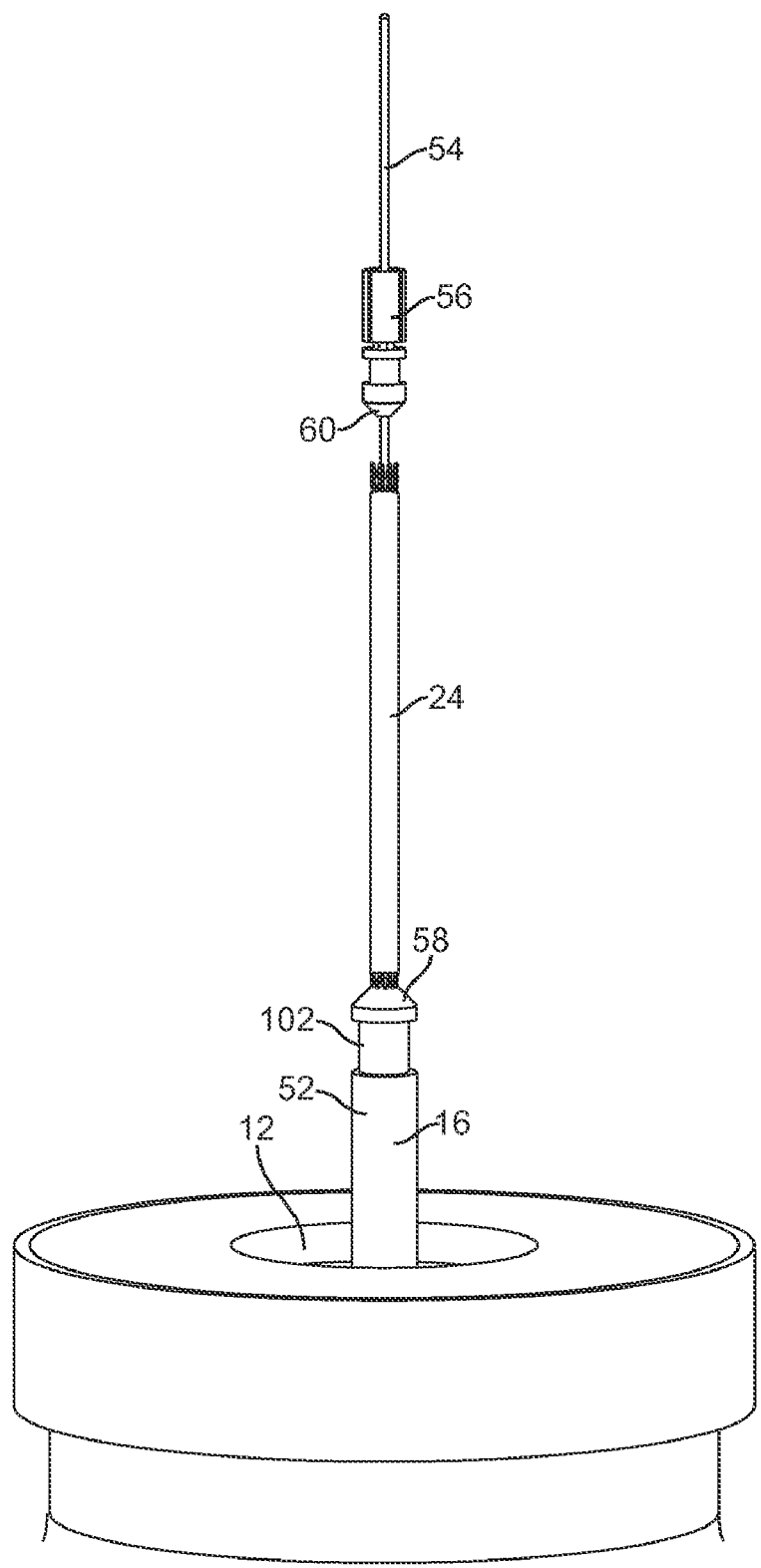
FIG. 8 is a perspective view of a stent and a stent support mounted vertically in a stent support receptacle.

Next the stent support 16 with the stent 24 mounted thereon is placed in a vertical position with the first support element 52 at a lower position and the second support element 56 at an upper position, as shown in FIG. 8. To hold the stent support 16 and stent 24 in the vertical position, the first support element 52 is placed in the stent support receptacle 12, and then a stent support holder 50 (FIG. 9) is used to hold the stent support 16 in a vertical position. The stent support holder 50 preferably includes a pair of grippers (FIG. 1) that are pivotably connected like a pair of scissors, each of the grippers having a V-shaped groove (FIG. 1) for receiving the stent support 16. The grippers can pivot open to receive the stent support 16 and pivot close to hold the stent support 16 in an opening formed by the V-shaped grooves. In this position, the lower end of the stent 24 rests on the conical portion 58 of the first support element 52 under the weight of the stent 24. The weight of the stent 24, acting on the conical portion 58 of the first support element 52, tends to center the lower end of the stent 24 around the core element 54.

At this point, the stent 24 may be re-seated to ensure that the stent 24 is properly seated on the conical portion 58 of the first support element 52. The stent 24 may be re-seated in several ways. For example, the stent 24 may be re-seated by vibrating the first support element 52 or lightly striking the first support element 52 to cause it to vibrate. Vibration of the first support element 52 tends to cause the stent 24 to be properly seated on the conical portion 58 of the first support element 52. Alternatively, the stent 24 may be re-seated by lifting the stent 24 off the first support element 52 and releasing the stent 24. Furthermore, the stent 24 may be re-seated by manipulating the stent 24, such as lightly tapping on the stent 24.

Figure 9:
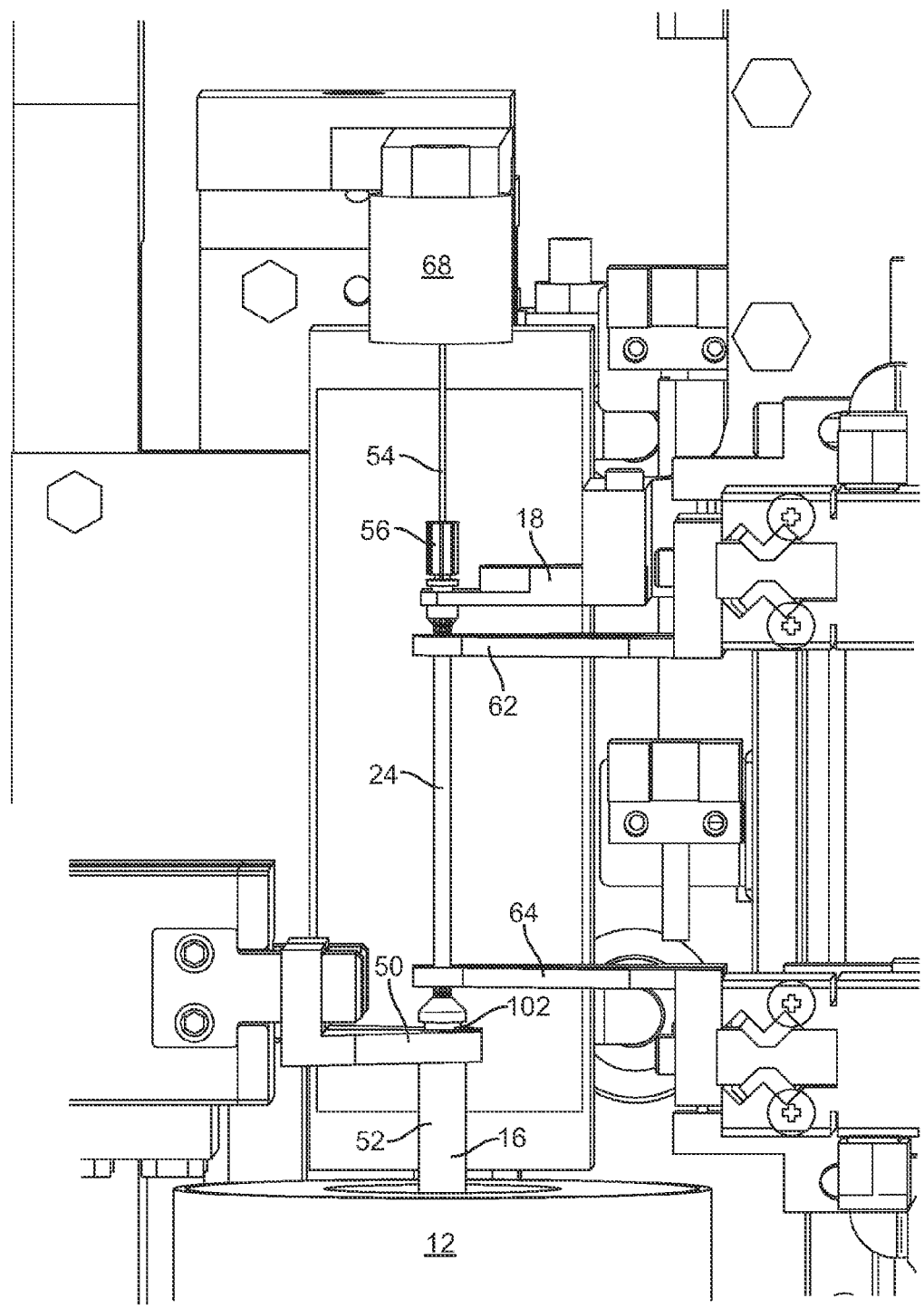
FIG. 9 is a perspective view of the free end of a core element being supported by a first core element support.

In addition, as shown in FIGS. 1 and 9, the device 10 may have two stent holders 62, 64 that can be used to hold and center the stent 24 around the core element 54 of the stent support 16. Preferably, one of the stent holders 62, 64 holds and centers the top portion of the stent 24, and the other holder holds and centers the bottom portion of the stent 24. Each stent holder 62, 64 preferably includes a pair of grippers (FIG. 1) that are pivotably connected like a pair of scissors, each of the grippers having a V-shaped groove (FIG. 1) for holding the stent 24. The grippers can pivot open to receive the stent 24 and pivot close to hold the stent 24 in an opening formed by the V-shaped grooves.

When the stent support 16 and stent 24 are placed in a vertical position, the free end of the core element 54 preferably is centered and fixed to a point on the axis of the first support element 52 to ensure that the core element 54 is straight and coincides with the axis of the first support element 52. When its free end is not centered, the core element 54, due to its flexibility, may not always be straight and coincide with the axis of the first support element 52. This makes it difficult to measure stent runout as the position of the stent 24 is caused by both stent runout and the position of the core element 54. Separating the effects of stent runout and core element position may be difficult. Additionally, when the first support element 52 is rotated to produce a 360° digital image of the stent's outer surface, the core element 54 and the stent 24 may oscillate about the axis of the first support element 52. This oscillation makes it difficult to produce a high-quality digital image of the stent's outer surface.

Figure 10:
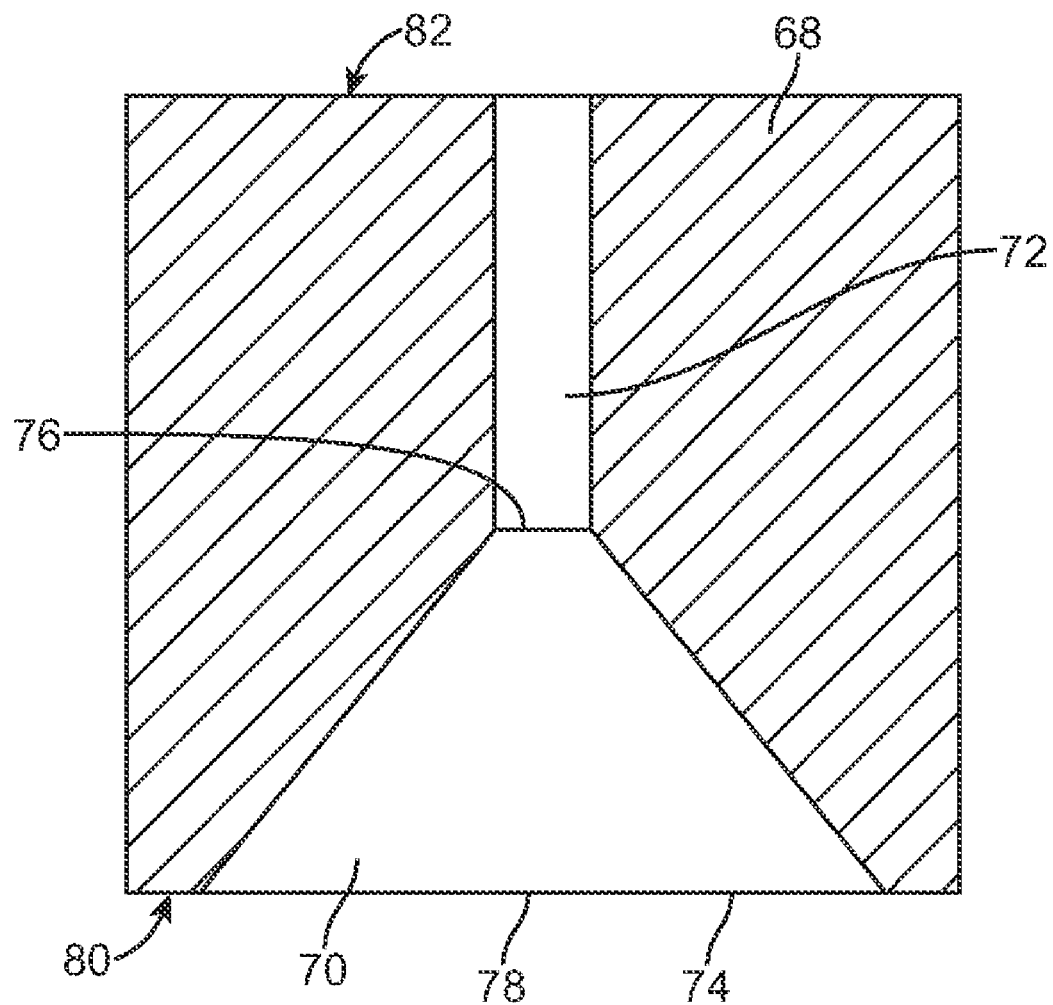
FIG. 10 is a cross-sectional view of the first core element support.

The centering of the free end of the core element 54 may be accomplished in any suitable way. For example, a core element support 68, as shown in FIG. 9, can be used to center the free end of the core element 54. The core element support 68 preferably has a cylindrical configuration and includes a conical inner cavity 70 and a bore 72, as shown in FIG. 10. The conical cavity 70 has a base 74 and an apex 76, wherein the base 74 defines an opening 78 on the bottom end surface 80 of the cylindrical support 68. Preferably, the bore 72 extends coaxially from the apex 76 of the conical cavity 70 to the top end surface 82 of the cylindrical support 68.

In the device 10, as shown in FIG. 9, the core element support 68 preferably is positioned so that the axis of the conical cavity 70 and bore 72 coincides with the axis of the first support element 52. Additionally, the core element support 68 preferably is able to move along the axis of the first support element 52.

During operation, after the stent support 16 and stent 24 are placed in a vertical position, the core element support 68 starts moving from a position above the free end of the core element 54 towards to the free end of the core element 54 with the opening 78 facing the free end of the core element 54. This movement of the support 68 allows the opening 78 of the support 68 to capture the free end of the core element 54 and allows the conical cavity 70 to guide the free end into the bore 72. Preferably, the bore 72 is sufficiently small such that the free end of the core element 54 preferably is centered and fixed to a point on the axis of the first support element 52 and such that the core element 54 is straight and coincides with the axis of the first support element 52. The opening 78 preferably is sufficiently large that it can always capture the free end of the core element 54.

Figure 11:
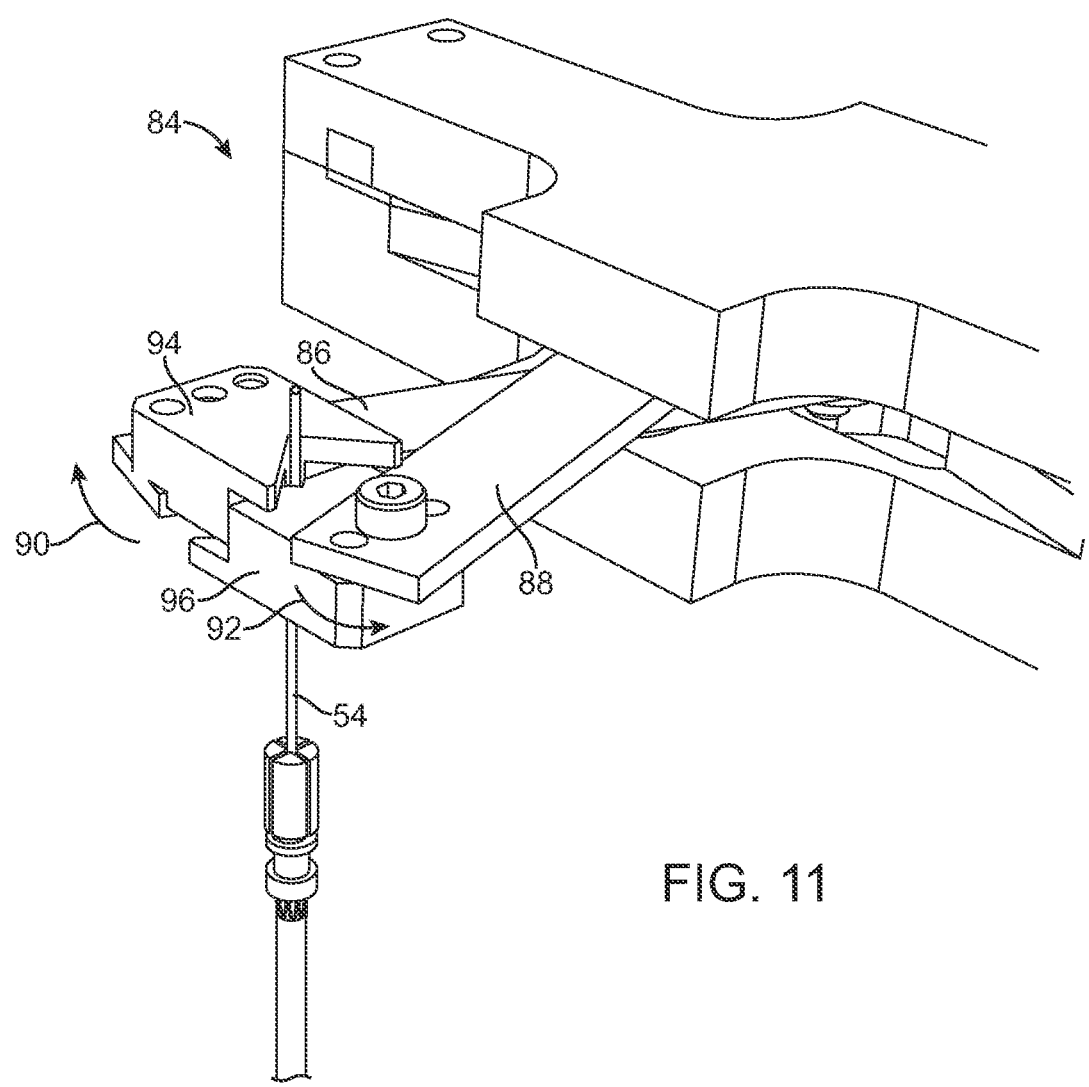
FIG. 11 is a perspective view of a second core element support.

Alternatively, as shown in FIG. 11, the free end of the core element 54 may be supported by a different core element support 84. The core element support 84 includes a scissor-like mechanism with two pivotable flat bars 86, 88 that can pivot as shown by arrows 90, 92, respectively. Clamps 94, 96 with opposing wedge-shaped cutout sections are coupled to the distal ends of the pivotable flat bars 86, 88, respectively. The free end of the core element 54 is clamped at the apices of the opposing wedge-shaped cutout sections but can still rotate. With this arrangement, the stent support 16 can rotate without much oscillation of the core element 54.

After the stent support 16 and stent 24 have been properly positioned, a digital image of the vertically-positioned stent support 16 and stent 24 is taken with the digital imaging device 20. The device 10 shown in FIG. 1 may include a backlight 22 (FIG. 1) for illuminating the stent support 16 and stent 24 in silhouette to improve the quality of the digital image. The device 10 may also include one or more reflecting members 98 such as mirrors that reflect the image of the stent support 16 and stent 24 into the lens of the imaging device 20, so that the imaging device 20 does not need to directly face the stent support 16 and stent 24. The digital image of the stent support 16 and stent 24 is then analyzed by the computer 14 to compute the vertical position of the stent's upper end. Based on the computed vertical position of the stent's upper end, the computer 14 can compute a desired position of the second support element 56.

The relationship between the position of the stent's upper end and the desired position of the second support element 56 may be determined experimentally. For example, for a given position of the stent's upper end, the second support element 56 may be placed at various positions, and the stent runout is computed by the computer 14 for each of these positions. Each position of the second support element that produces an acceptable stent runout can be designated as an acceptable position. The position that produces the smallest stent runout may be designated as the desired position. This process, repeated for all positions of the stent's upper end, establishes a relationship between the position of the stent's upper end and the desired position of the second support element 56. This relationship can be used to compute the desired position of the second support element 56 based on the vertical position of the stent's upper end. Preferably, the positioning device 18 used to position the second support element 56 at the desired position is sufficiently precise that the second support element 56 is consistently positioned at the desired position or at least at an acceptable position.

After the desired position of the second support element 56 has been obtained, the positioning device 18 is used to move the second support element 56 from its original position to the desired position. As the second support element 56 is advanced towards the stent 24, the conical sections 58, 60 of the first and second support elements 52, 56 engage the respective ends of the stent 24 to center the stent 24 around the core element 54 and to secure the stent 24 in the longitudinal direction of the stent support 16. The interference fit between the second support element 56 and the core element 54 ensures that the second support element 56 and stent 24 remain assembled and properly aligned during subsequent handling, processing and coating.

Figure 12:
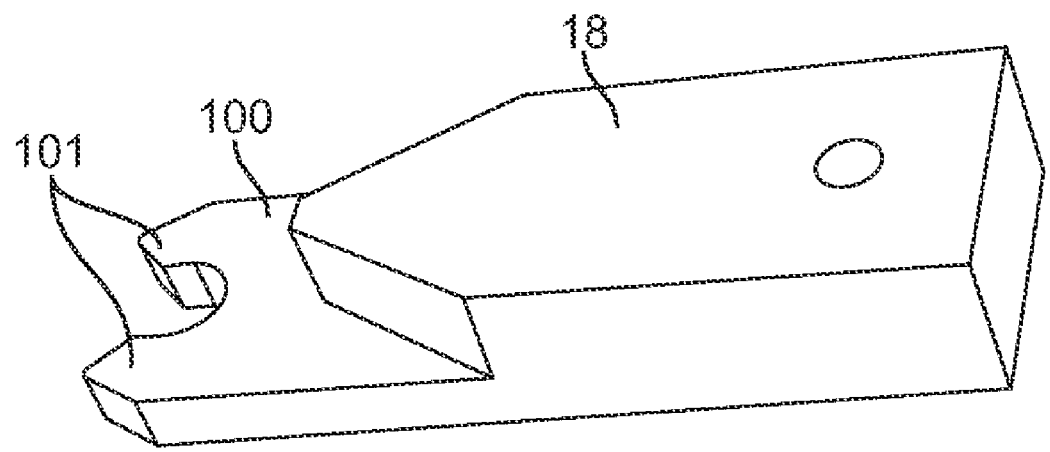
FIG. 12 is a perspective view of a positioning device.

In the preferred embodiment, the positioning device 18 includes a fork member 100, as shown in FIG. 12. When the positioning device 18 is used to move the second support element 56, the fork member 100 extends into a circumferential groove 102 of the second support element 56. Preferably, the distance between the legs 101 of the fork member 100 is greater than the diameter of the groove 102, so that the fork member 100 is free to move up and down in the groove 102. However, the distance between the legs 101 of the fork member 100 preferably is less than the diameter of the second support element 56.

To move the second support element 56 downwards, the fork member 100 engages the lower side surface of the groove 102. And to move the second support element 56 upwards, the fork member 100 engages the upper side surface of the groove 102. This arrangement is advantageous because, as long as the position and dimensions of the groove 102 and the dimensions of the fork member 100 are given, the relative position between the second support element 56 and the positioning device 18 can be precisely determined. As a result, the position of the second support element 56 can be calculated from the position of the positioning device 18 and can be controlled by controlling the position of the positioning device 18.

Figure 13:
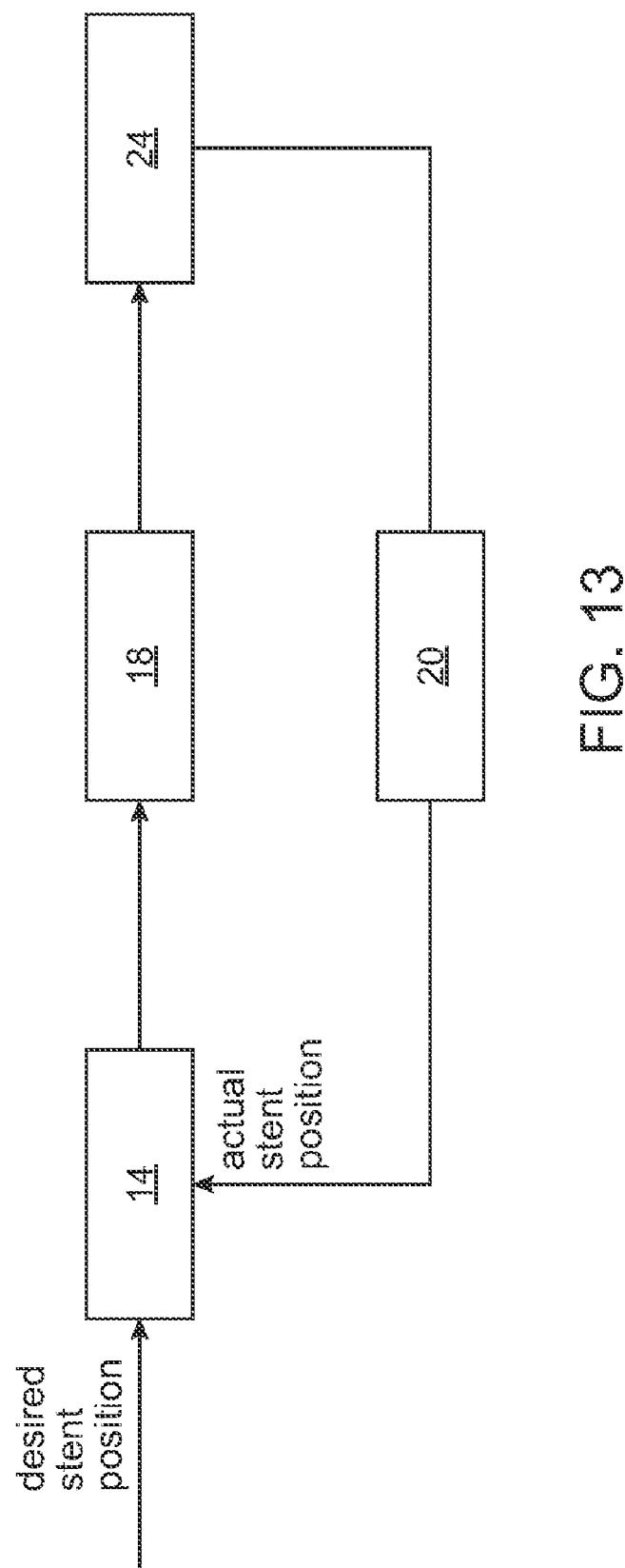
FIG. 13 is a schematic diagram showing a feedback control loop for controlling the position of the second support element of the stent support.

After the stent 24 has been mounted on the stent support 16, a second digital image of the stent support 16 and stent 24 may be taken to determine whether the second support element 56 is sufficiently close to the desired position. The computer 14 can compute the actual position of the second support element 56 from the second digital image and compare with the desired position. If the difference between the actual and desired positions exceeds an acceptable limit, the second support element 56 can be re-positioned. This process forms a feedback control loop, as shown in FIG. 13, and can be repeated until the difference is within the acceptable limit. Alternatively, after several unsuccessful attempts the stent 24 and stent support 16 can be discarded as defective.

Alternatively or additionally, stent runout may be used to determine whether the second support element 56 is properly positioned. If the stent runout is above an acceptable limit, the second support element 56 is considered to be improperly positioned, and the stent 24 may be remounted or discarded as defective.

Figure 14:
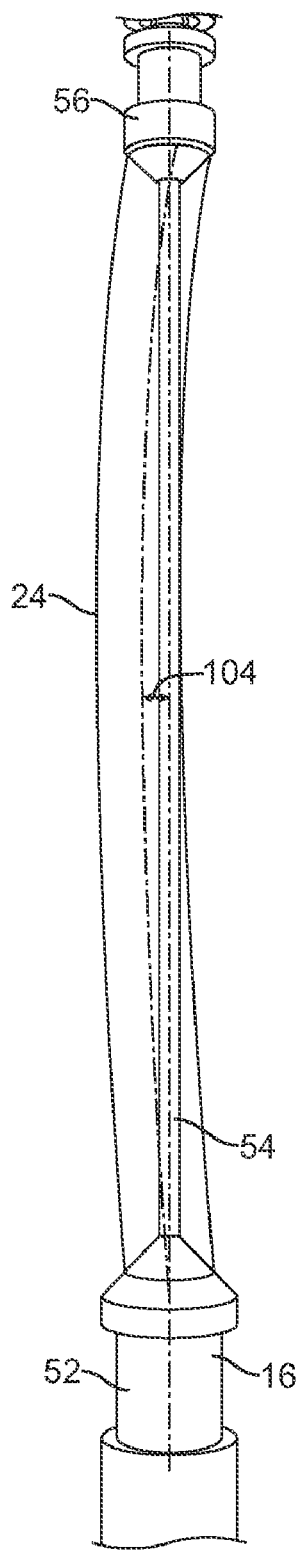
FIG. 14 is a view of a stent mounted on a stent support with stent runout.

Stent runout can be variously defined. As shown in FIG. 14, the stent runout can be defined as the radial distance 104 between the axis of the stent 24 and the axis of the core element 54. Since this distance 104 may vary along the axis of the core element 54, stent runout can be defined as the average or mean radial distance along the axis of the core element 54 or the maximum radial distance.

Stent runout may be determined in various manners. For example, stent runout can be determined from one or more digital images of the stent support 16 and stent 24. Often, however, stent runout cannot be accurately determined by taking a single digital image of the stent support 16 and stent 24. For example, if the direction of the stent runout happens to be perpendicular to the digital image, the runout cannot be detected at all from the digital image. Only when the direction of the stent runout is parallel to the digital image, stent runout cannot be accurately determined from the single digital image. Therefore, it is desirable to use two or more images of the stent support 16 and stent 24 to determine stent runout. In a preferred embodiment, a digital image of the stent support 16 and stent 24 is taken every 1° to 90° stent rotation for at least 180° of stent rotation, and stent runout is determined from the digital images. For example, a digital image of the stent support 16 and stent 24 may be taken every 5° of stent rotation for 180° or 360°. In many cases, the true stent runout is the maximum stent runout detected from the digital images.

Figure 15:
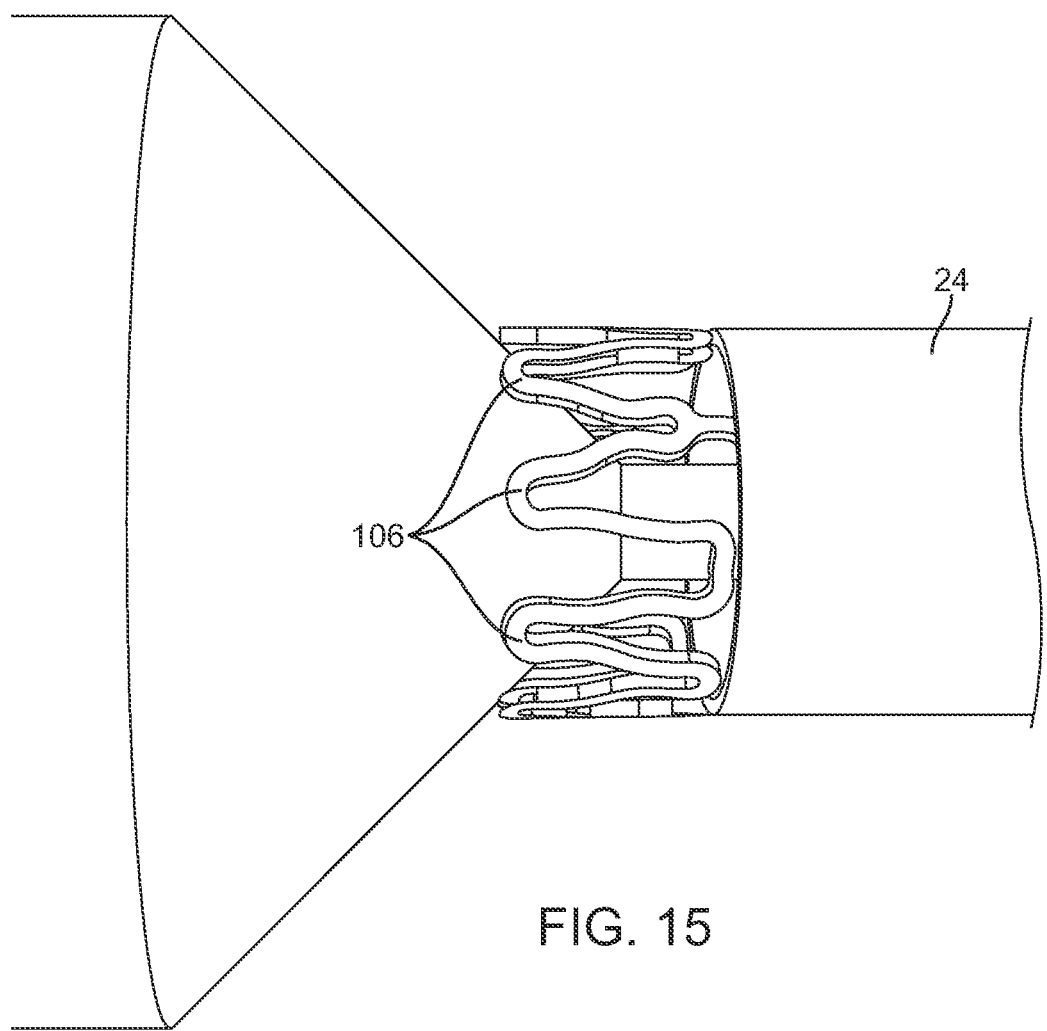
FIGS. 15 and 16 are perspective views of crowns at a stent end.
Figure 16:
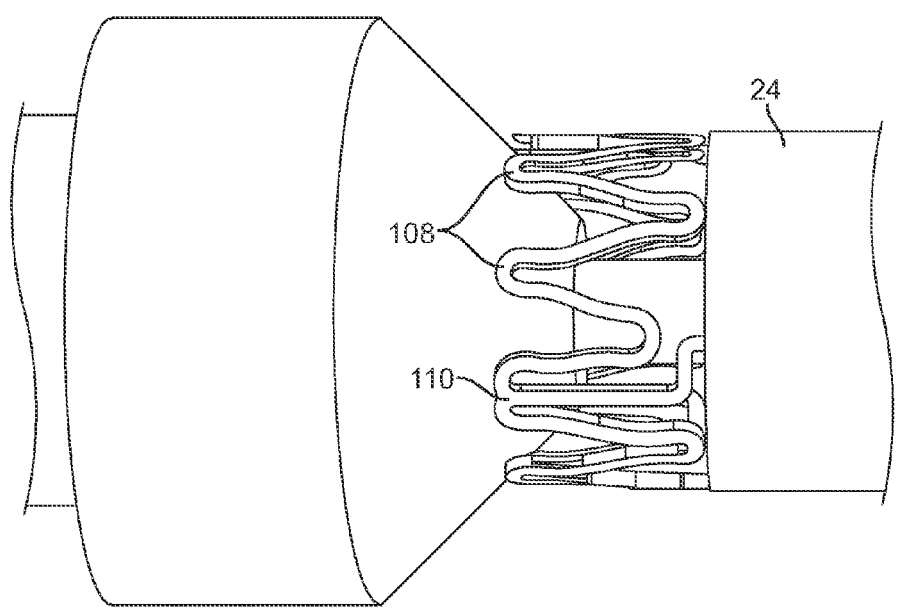

Since a stent manufacturer often makes more than one type of stents, it may be desirable in some cases to verify that the proper type of stent is mounted on the stent support 16. The stent type may be determined from a digital image of the stent 24 in various manners. For example, if the different types of stents have different lengths, the length of a stent 24 can be computed from the digital image and can be used to determine the type of stent mounted on the stent support 16. The length of the stent 24 can be determined by measuring the distance between the two ends of the stent 24. Alternatively, if one end of the stent 24 is always at the same position, the stent length can be computed from the position of the other end. If the different types of stents have different end crowns 106 (FIG. 15), the stent type can be determined from the number of end crowns 106 at a stent end. The number of end crowns 106 can be determined from a 360° digital image of the stent's outer surface. If the different types of stents have different types of end crowns, the stent type can also be determined from the types of end crowns at a stent end. For example, an end of one type of stent may have four U-shaped end crowns 108 (FIG. 16) and five W-shaped end crowns 110 (FIG. 16), and an end of another type of stent may have six U-shaped end crowns 108 and three W-shaped end crowns 110. In some cases, two or more of these stent features may be used together to determine stent types.

The different types of end crowns 108, 110 may also be used to determine the orientation of the stent 24. For example, a first end of a stent may have all U-shaped end crowns 108, and a second end may have four U-shaped end crowns 108 and five W-shaped end crowns 110. If the second end of the stent should be the upper end of the stent 24 facing the second support element 56, the types of end crowns 108, 110 at a stent end can be inspected to ensure that the stent 24 is properly oriented.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A method for aligning a stent with a stent support, comprising:
 placing a stent support and a stent mounted on the stent support in a vertical position with the stent support's first support element at a lower position and the stent support's second support element at an upper position, wherein the lower end of the stent faces a conical portion of the first support element and the upper end of the stent faces a conical portion of the second support element;
 obtaining a digital image of the stent support and stent;
 analyzing the digital image of the stent support and stent to compute the vertical position of the stent's upper end;
 computing a desired position of the second support element based on the position of the stent's upper end; and
 using a positioning device to move the second support element to the desired position, wherein the movement of the second support element causes the conical portions of the first and second support elements to engage the respective ends of the stent to center the stent around a core element of the stent support and to secure the stent in a longitudinal direction of the stent support.

2. The method of claim 1, further comprising:
 the step of obtaining the digital image of the stent support and stent includes using a digital imaging device to obtain the digital image of the stent support and stent.

3. The method of claim 1, further comprising:
 computing stent runout after the step of using the positioning device to move the second support element.

4. The method of claim 3, further comprising:
 if the computed stent runout is greater than an acceptable limit, lifting the second support element to disengage the second support element from the upper end of the stent.

5. The method of claim 4, further comprising:
 after the second support element has been disengaged from the upper end of the stent, repeating the step of obtaining a digital image of the stent support and stent;
 repeating the step of analyzing the digital image;
 repeating the step of computing a desired position of the second support element; and
 repeating the step of using the positioning device to move the second support element to the desired position.

6. The method of claim 1, further comprising:
 obtaining a second digital image of the stent support and stent after the step of using the positioning device to move the second support element; and
 computing the actual position of the second support element from the second digital image and comparing the actual position of the second support element with the desired position.

7. The method of claim 6, further comprising:
 if the difference between the actual and desired positions of the second support element exceeds an acceptable limit, using the positioning device to move the second support element to the desired position.

8. The method of claim 1, further comprising:
 re-seating the stent on the conical portion of the first support element before the step of obtaining the digital image of the stent support and the stent.

9. The method of claim 8, wherein the step of re-seating includes vibrating the first support element.

10. The method of claim 8, wherein the step of re-seating includes striking the first support element.

11. The method of claim 8, wherein the step of re-seating includes lifting the stent off the first support element and releasing the stent.

12. The method of claim 8, wherein the step of re-seating includes tapping on the stent.

13. The method of claim 1, further comprising determining the orientation of the stent from the digital image of the stent support and stent.

14. The method of claim 13, wherein the step of determining the orientation of the stent includes examining crown types at least one stent end.

15. The method of claim 1, further comprising determining the type of the stent from the digital image of the stent support and stent.

16. The method of claim 15, further comprising computing the length of the stent and determining the type of the stent based on the length of the stent.

17. The method of claim 15, further comprising computing the number of end crowns at least one of the stent ends and determining the type of the stent based on the number of end crowns.

18. The method of claim 15, further comprising determining the types of end crowns at least one of the stent ends and determining the type of the stent based on the types of end crowns.

19. The method of claim 15, further comprising:
 determining the types of end crowns at least one of the stent ends;
 computing the length of the stent; and
 determining the type of the stent based on the types of end crowns and the length of the stent.

20. The method of claim 1, wherein the digital image includes the entire outer surfaces of the stent ends.

21. The method of claim 20, further comprising determining the orientation of the stent from the digital image of the stent support and stent.

22. The method of claim 21, wherein the step of determining the orientation of the stent includes examining the end crown types at least one stent end.

23. The method of claim 20, further comprising determining the type of the stent from the digital image of the stent support and stent.

24. The method of claim 23, further comprising computing the length of the stent and determining the type of the stent based on the length of the stent.

25. The method of claim 23, further comprising determining the number of end crowns at least one of the stent ends and determining the type of the stent based on the number of end crowns.

26. The method of claim 23, further comprising determining the types of end crowns at least one of the stent ends and determining the type of the stent based on the types of end crowns.

27. The method of claim 23, further comprising:
   determining the types of end crowns at least one of the stent ends;
   computing the length of the stent; and
   determining the type of the stent based on the types of end crowns and the length of the stent.

28. The method of claim 1, further comprising:
   supporting a free end of the core element so that the core element and the first support element are substantially coaxial.

29. A device for aligning a stent with a stent support, comprising:
   a stent support receptacle for receiving a first support element of a stent support to position the stent support in a vertical position;
   a digital imaging device for imaging a stent mounted on the stent support;
   a computer connected to the digital imaging device for receiving a digital image of the stent support and the stent mounted thereon, wherein the computer computes the position of an upper end of the stent from the digital image of the stent support and the stent mounted thereon and computes a desired position of a second support element of the stent support based on the position of the stent's upper end; and
   a positioning device for moving the second support element to the desired position.

30. The device of claim 29, further comprising:
   a core element support for supporting a free end of a core element of the stent support so that the core element and the first support element are substantially coaxial.

\* \* \* \* \*